(12) United States Patent
Lukin et al.

(10) Patent No.: US 8,519,186 B2
(45) Date of Patent: Aug. 27, 2013

(54) PROCESS FOR THE PREPARATION OF INDAZOLYL UREAS THAT INHIBIT VANILLOID SUBTYPE 1 (VR1) RECEPTORS

(75) Inventors: Kirill A. Lukin, Vernon Hills, IL (US); Margaret Chi-Ping Hsu, Lake Forest, IL (US); Dilinie P. Fernando, Groton, CT (US); Brian J. Kotecki, Oak Creek, WI (US); Marvin R. Leanna, Grayslake, IL (US)

(73) Assignee: AbbVie Inc., North Chicago, IL (US)

( * ) Notice: Subject to any disclaimer, the term of this patent is extended or adjusted under 35 U.S.C. 154(b) by 324 days.

(21) Appl. No.: 12/914,645

(22) Filed: Oct. 28, 2010

(65) Prior Publication Data

US 2011/0040102 A1 Feb. 17, 2011

Related U.S. Application Data

(62) Division of application No. 11/734,900, filed on Apr. 13, 2007, now Pat. No. 7,847,104.

(60) Provisional application No. 60/792,099, filed on Apr. 14, 2006.

(51) Int. Cl.
*C07C 275/26* (2006.01)

(52) U.S. Cl.
USPC .......................................................... 564/47

(58) Field of Classification Search
None
See application file for complete search history.

(56) References Cited

U.S. PATENT DOCUMENTS

| | | | |
|---|---|---|---|
| 4,051,252 | A | 9/1977 | Mayer et al. |
| 5,905,080 | A | 5/1999 | Duckworth et al. |
| 7,015,233 | B2 | 3/2006 | Gomtsyan et al. |
| 2005/0043351 | A1 | 2/2005 | Gomtsyan et al. |
| 2005/0267096 | A1 | 12/2005 | Allerton et al. |
| 2007/0021450 | A1* | 1/2007 | Sklarz et al. ............ 514/269 |

FOREIGN PATENT DOCUMENTS

| | | |
|---|---|---|
| GB | 1054833 A | 1/1967 |
| JP | 41004583 B | 3/1966 |
| JP | 51082266 A | 7/1976 |
| JP | 2005533014 | 11/2005 |
| JP | 2009505980 A | 2/2009 |
| JP | 2009511557 A | 3/2009 |
| WO | WO03035065 A1 | 5/2003 |
| WO | 03091225 A1 | 11/2003 |
| WO | 2004113304 A1 | 12/2004 |
| WO | WO2007021937 A2 | 2/2007 |
| WO | 2007042806 A1 | 4/2007 |
| WO | WO2007056023 A2 | 5/2007 |
| WO | WO2007062996 A1 | 6/2007 |
| WO | WO2007021937 A3 | 7/2007 |
| WO | WO2007056023 A3 | 10/2007 |

OTHER PUBLICATIONS

Barluenga, Jose et al., "Palladium catalyzed alkenyl amination: from enamines to heterocyclic synthesis," Chem. Commun., pp. 4891 4901, 2005.
Greene T.W., et al., "Protection for the Amino group," Protective Groups in Organic Synthesis, 1999, Third Edition, pp. 494-653.
Inoue, Yoshio et al., "Direct N-Allylation of Amides with 2-Allylisourea Catalyzed by Palladium(0)," Bull. Chem. Soc. Jpn., vol. 58, pp. 2721-2722, 1985.
International Search Report for application No. PCT/US07/066605, Mailed on Feb. 10, 2008, 1 page.
Opposition filed by "Asociacion de Laboratorios Farmaceuticos, Alafar" received from Ecuadorian Patent Office, through Providence notified on Apr. 1, 2009, 3 pages.
Artamkina A., et al., "Palladium-Catalyzed Reaction of Aryl Halides with Urea," Tetrahedron Letters, 2001, vol. 42, pp. 4381-4384.
Auwers K.V., et al., "Ober Wanderung Von Acylon Bei Indazolderivaton," 1927, vol. 451, pp. 282-307.
Guram et al., "Palladium-Catalyzed Aromatic Aminations with in Situ Generated Aminostannanes," J. Am. Chem. Soc., 116:7901 (1994).
Hamann et al., "Sterically Hindered Chelating Alkyl Phosphines Provide Large Rate Accelerations in Palladium-Catalyzed Amination of Aryl Iodides, Bromides, and Chlorides, and the First Amination of Aryl Tosylates," J. Am. Chem. Soc., 120:7368-7370 (1998).
Kawatsura et al., "Simple, Highly Active Palladium Catalysts for Ketone and Malonate Arylation: Dissecting the Importance of Chelation and Steric Hindrance," J. Am. Chem. Soc., 121: 1473-1478 (1999).
Lloyd-Jones, "Palladium-Catalyzed α-Arylation of Esters: Ideal New Methodology for Discovery Chemistry," ACIEE, 41:953-956 (2002).
Mangion, "Buchwald-Hartwig Chemistry," Internet Slides dated Jul. 30, 2002, http://www.princeton.edu/chemistry/macmillan/group-meetings/powerpoint-ian-buchhart.pdf.
Old et al., "A Highly Active Catalyst for Palladium-Catalyzed Cross-Coupling Reactions; Room-Temperature Suzuki Couplings and Amination of Unactivated Aryl Chlorides," J. Am. Chem. Soc., 120: 9722-9723 (1998).
Vogl et al., "Palladium-Catalyzed Monoarylation of Nitroalkanes," J. Org. Chem., 67:106-111 (2002).
Wolfe et al., "An Ammonia Equivalent for the Palladium-Catalyzed Amination of Aryl Halides and Triflates," Tet. Lett., 38:6367-6370 (1997).

* cited by examiner

*Primary Examiner* — Kamal Saeed

(57) ABSTRACT

The present invention relates to a process of preparing indazolyl ureas that are useful as antagonists of the vanilloid receptor subtype 1 (VR1).

2 Claims, No Drawings

PROCESS FOR THE PREPARATION OF INDAZOLYL UREAS THAT INHIBIT VANILLOID SUBTYPE 1 (VR1) RECEPTORS

This application is a divisional of U.S. patent application Ser. No. 11/734,900 filed on Apr. 13, 2007, which claims priority to the U.S. provisional application Ser. No. 60/792,099 filed on Apr. 14, 2006.

FIELD OF THE INVENTION

The invention relates to the process of preparing indazolyl ureas that are useful as Vanilloid subtype 1 receptor (VR1) inhibitors. The invention also relates to the intermediates in the process that generates the indazolyl ureas and uses thereof.

BACKGROUND

Compounds of general formula (I) that are antagonists of the Vanilloid subtype 1 receptor (VR1) were originally prepared via a synthetic route described in U.S. Ser. No. 10/864,068. The synthetic route in this invention relied upon treating a nitroanaline with sodium nitrite to form a nitroindazole intermediate. Recent developments have afforded a new highly efficient synthetic pathway, which generates fewer impurities and presents a more cost effective process for generating this valuable compound. The new route also incorporates the following innovative chemical methods: a new method for the preparation of 4-haloindazoles via condensation of the corresponding halogenated benzaldehydes or certain halogenated ketone substituted benzene rings with hydrazine; a method for the selective protection of haloindazoles at the N1 or N2 position and a method for the conversion of haloindazoles into indazoyl ureas.

Compounds of general formula (I) that are antagonists of the Vanilloid subtype 1 receptor (VR1) are useful in treating disorders associated with overactivity of the Vanilloid subtype 1 receptor a described in U.S. Ser. No. 10/864,068.

DETAILED DESCRIPTION OF THE INVENTION

The present invention discloses a novel process to make compounds of formula (I),

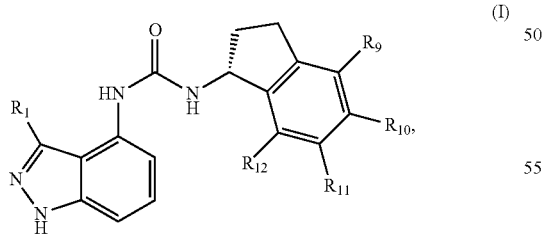

wherein, $R_1$ is selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C-$, $R_B(SO)_2R_AN-$, $R_AO(SO)_2-$, $R_BO(SO)_2-$, $Z_AZ_BN-$, $(Z_AZ_BN)$alkyl, $(Z_AZ_BN)$carbonyl, $(Z_AZ_BN)$carbonylalkyl, and $(Z_AZ_BN)$sulfonyl;

$R_9$, $R_{10}$, $R_{11}$, and $R_{12}$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, aryl, carboxy, carboxyalkyl, cyano, cyanoalkyl, formyl, formylalkyl, haloalkoxy, haloalkyl, haloalkylthio, halogen, heteroaryl, heterocycle, hydroxy, hydroxyalkyl, mercapto, mercaptoalkyl, nitro, $(CF_3)_2(HO)C-$, $R_B(SO)_2R_AN-$, $R_AO(SO)_2-$, $R_BO(SO)_2-$, $Z_AZ_BN-$, $(Z_AZ_BN)$alkyl, $(Z_AZ_BN)$carbonyl, $(Z_AZ_BN)$carbonylalkyl, and $(Z_AZ_BN)$sulfonyl;

$R_A$ is hydrogen or alkyl;

$R_B$ is alkyl, aryl, or arylalkyl; and $Z_A$ and $Z_B$ are each independently hydrogen, alkyl, alkylcarbonyl, formyl, aryl, or arylalkyl, comprising the steps of:

(a) heating a mixture of a compound of formula (III), a base selected from the group consisting of sodium hydroxide, potassium phosphate and cesium carbonate, and a composition comprising a compound of formula (IIa), a compound of formula (IIb) or a mixture thereof, wherein P is selected from the group consisting of alkoxyalkyl, alkylcarbonyl, alkoxycarbonyl, arylalkyl, arylcarbonyl and aryloxycarbonyl, $R_1$ is defined under the compound of formula (I) and Y is chloro or bromo, in the presence of palladium catalyst and a phosphine based ligand,

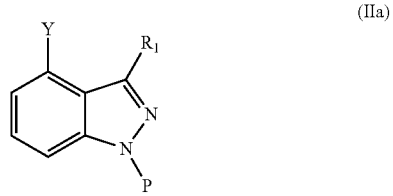

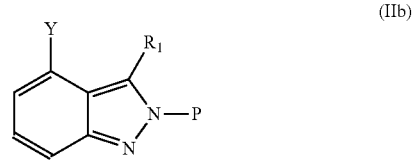

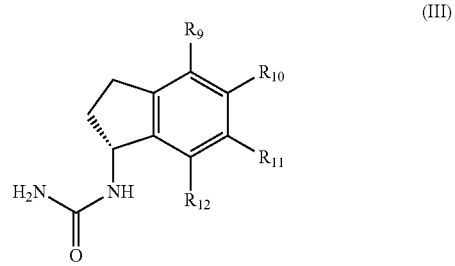

to provide a composition consisting of a compound of formula (IVa), a compound of formula (IVb) or a mixture thereof, wherein $R_1$, $R_9$, $R_{10}$, $R_{11}$, and $R_{12}$ are defined under the compound of formula (I),

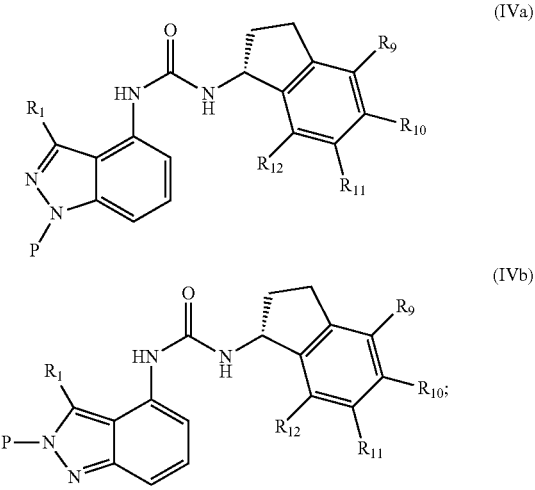

(IVa)

(IVb)

followed by (b) treating the composition consisting of the compound of formula (IVa), the compound of formula (IVb) or the mixture thereof, to conditions that will provide the compound of formula (I). Compounds of formula (I) are useful for controlling pain and urinary disorders in mammals by inhibiting the VR1 receptor.

It is understood that the process of this invention can be carried out in an inert atmosphere, preferably nitrogen. Contained within the scope of this invention, it is understood that there are several palladium catalysts which may be utilized in step (a) which include but are not limited to palladium acetate and $Pd_2(DBA)_3$. It is understood that within the scope of this invention, the phosphine based ligand may include phosphine ligands that are utilized by one skilled in the art of coupling reactions of this type. Most preferred phosphine ligands include but are not limited to Xantphos, 2-di-t-butylphosphino-1-1'-binaphthyl and 5-(di-t-butylphosphanyl)-1',3',5'-triphenyl-1'H-[1,4']bipyrazolyl. It is also understood that in the process of this invention, the base of step (a) can be potassium phosphate, potassium carbonate or cesium carbonate, preferably cesium carbonate.

It is also understood that in the process of this invention, the mixture of step (a) is heated to reflux for 2-20 hours, in an organic solvent including but not limited to THF, toluene, DMF, NMP or ethylene glycol dimethyl ether, preferably ethylene glycol dimethyl ether. In certain embodiments, wherein Y is bromo, the mixture of step (a) is generally heated for about 2 to about 10 hours in ethylene glycol dimethyl ether. In some instances, when Y is bromo, the mixture of step (a) is heated for about 5 hours. In certain embodiments, wherein Y is bromo, the preferred conditions include the use of $Pd_2(DBA)_3$, Xantphos and cesium carbonate in step (a).

In other embodiments, wherein Y is chloro, the mixture of step (a) is generally heated for about 5 to about 20 hours in ethylene glycol dimethyl ether. When Y is chloro the preferred palladium catalyst is palladium acetate. In certain embodiment of the present invention wherein Y is chloro, there is disclosed the use of palladium acetate, 2-di-t-butylphosphino-1-1'-binaphthyl and potassium phosphate in step (a). These steps are generally followed by filtration and/or precipitation to provide the composition consisting of the compound of formula (IVa) or (IVb) or a mixture thereof.

The present invention also includes a process to prepare compound of formula (IIa) and compound of formula (IIb) as described in Scheme 1. Contained within an embodiment describing the process for the preparation of the compound of formula (IIa) and the compound of formula (IIb) outline the step (a), wherein the treatment of a meta-chloro or meta-bromo fluorobenzene with a base such as but not limited to lithium diisopropylamide, lithium dicyclohexyamide or lithium bis(trimethylsilyl)amide in a solvent is carried out between a temperature of about −50° C. to about −78° C. for about 1 to about 3 hours. The process further comprises treating the cold mixture with a compound of formula $R_1C(=O)—X$, wherein $R_1$ is hydrogen, alkenyl or alkyl, and X is chloro, $(CH_3)_2N—$, phenoxy, or nitrophenoxy, to provide a compound of formula (V),

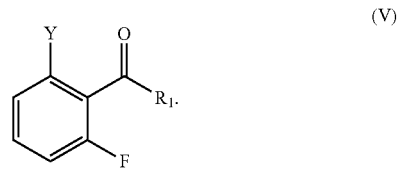

(V)

The process of the present invention further comprises the treatment of the compound of formula (V) with hydrazine in a solvent including but not limited to DMF, DMSO, or THF, preferably DMSO to obtain compounds of formula (VI),

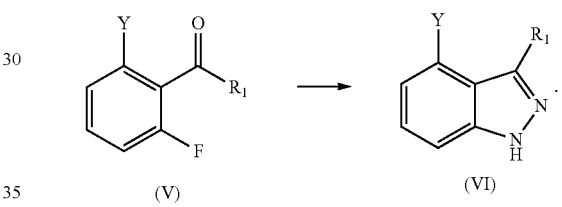

(V)                    (VI)

The process further comprises treating the compound of formula (VI) with a reagent P—Z, wherein P is selected from the group consisting of alkoxyalkyl, alkylcarbonyl, alkoxycarbonyl, arylalkyl, arylcarbonyl and aryloxycarbonyl, such as but not limited to acetyl chloride, acetic anhydride, benzyl bromide, benzyl chloroformate and di-tert-butyl dicarbonate, to provide the composition consisting of the compound of formula (IIa), the compound of formula (IIb) or a mixture of the compound of formula (IIa) and the compound of formula (IIb),

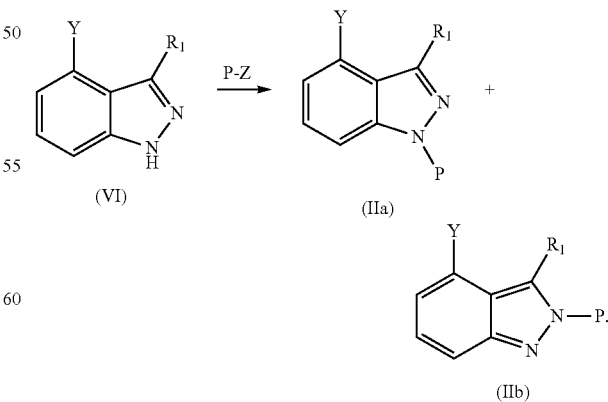

(VI)                    (IIa)

(IIb)

In one embodiment of the invention is disclosed the process which further comprises heating and stirring the mixture of the compound of formula (VI) and benzyl bromide in organic solvent, e.g N,N-dimethyl formamide, DMA, NMP, preferably DMF, to a temperature of about 40° C. to about 120° C. for the period of between about 4 hours and about 30 hours to introduce a benzyl protecting group onto one of the nitrogen atoms.

In another preferred embodiment, the process further includes treating the compound of formula (VI) with benzyl bromide in N,N-dimethyl formamide to a temperature of about 105° C. to about 115° C. for a period between about 20 hours to about 24 hours, to provide the compound of formula (VIIb),

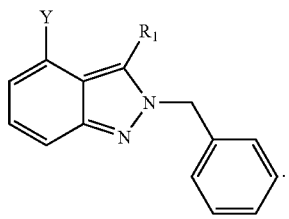

(VIIa)

In another embodiment, the process also discloses the heating and stirring the mixture of the compound of formula (VI) and benzyl bromide in N,N-dimethyl formamide to a temperature of about 50° C. to about 60° C. for a period between about 20 hours to about 24 hours to provide the compound of formula (VIIa),

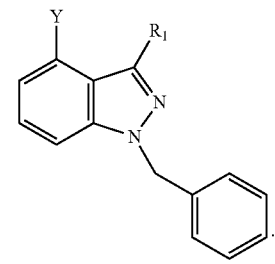

(VIIb)

The process of the present invention also discloses treating a compound of formula (VIII) as described in Scheme 3 to obtain a compound of formula (III),

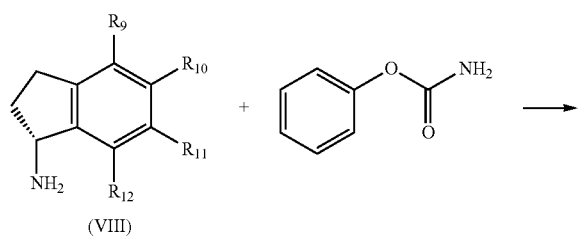

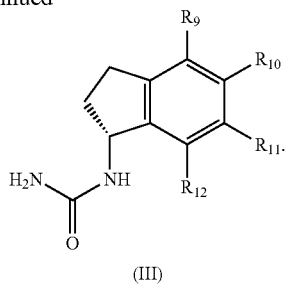

(III)

The process also describes treating the composition consisting of the compound of formula (VIIa), the compound of formula (VIIb) or the mixture thereof, wherein $R_1$ is defined under the compound of formula (I) and Y is chloro or bromo, with a compound of formula (III), a base selected from the group consisting of sodium carbonate, potassium carbonate and cesium carbonate, in the presence of palladium catalyst and a phosphine based ligand to provide a composition consisting of a compounds of formula (IVa), a compound of formula (IVb) or a mixture thereof, wherein the P group is benzyl. The process further describes treating the composition consisting of the compound of formula (IVa), the compound of formula (IVb) or the mixture thereof, wherein the P group is benzyl with a palladium catalyst comprising palladium on carbon, palladium hydroxide or palladium on barium sulfate, preferably palladium hydroxide, more preferably 20% palladium hydroxide and a hydrogen donor comprising an atmosphere of hydrogen, formic acid, or cyclohexadiene, preferably formic acid, in a solvent comprising an alcoholic solvents, tetrahydrofuran or ethyl acetate; preferably tetrahydrofuran to provide the compound of formula (I).

The present invention further includes a process for preparing the compound of formula (IX),

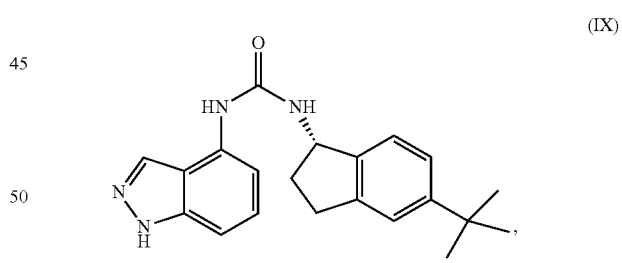

(IX)

comprising the steps of heating, preferably for 5-10 hours, a mixture of a compound of formula (XI), a base consisting of potassium phosphate, potassium carbonate or cesium carbonate, preferably cesium carbonate, and a composition consisting of the compound of formula (Xa), a compound of formula (Xb) or a mixture thereof, wherein Y is chloro or bromo, in the presence of a catalyst such as but not limited to $Pd_2(DBA)_3$ and a phosphine based ligand, including but not limited to Xantphos, 2-di-t-butylphosphino-1-1'-binaphthyl and 5-(di-t-butylphosphanyl)-1',3',5'-triphenyl-1'H-[1,4']bipyrazolyl under an atmosphere of nitrogen,

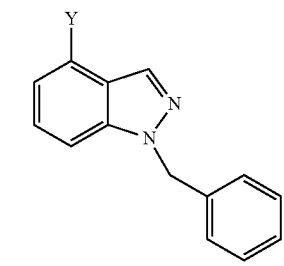

(Xa)

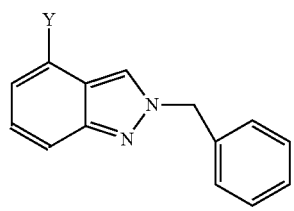

(Xb)

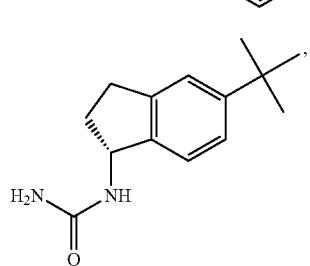

(XI)

to provide the composition consisting of a compound of formula (XIIa), a compound of formula (XIIb) or a mixture thereof,

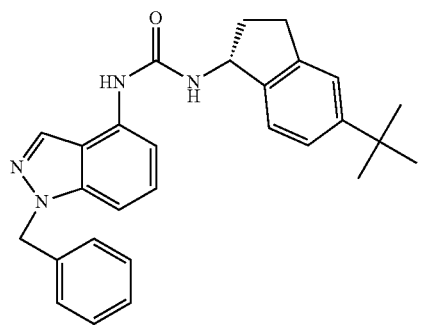

(XIIa)

(XIIb)

followed by treating the composition consisting of the compound of formula (XIIa), the compound of formula (XIIb) or the mixture thereof, with a palladium catalyst comprising palladium on carbon, palladium hydroxide or palladium on barium sulfate, preferably palladium hydroxide, more preferably 20% palladium hydroxide and a hydrogen donor comprising an atmosphere of hydrogen, formic acid, or cyclohexadiene, preferably formic acid, in a solvent comprising an alcoholic solvents, tetrahydrofuran or ethyl acetate; preferably tetrahydrofuran to provide the compound of formula (IX). The present invention includes a composition consisting of the compound of formula (IIa), the compound of formula (IIb), or the mixture thereof,

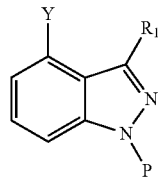

(IIa)

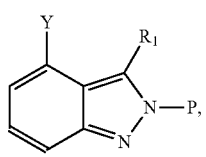

(IIb)

wherein Y is chloro or bromo; and $R_1$ is selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C-$, $R_B(SO)_2R_AN-$, $R_AO(SO)_2-$, $R_BO(SO)_2-$, $Z_AZ_BN-$, $(Z_AZ_BN)$alkyl, $(Z_AZ_BN)$carbonyl, $(Z_AZ_BN)$carbonylalkyl, or $(Z_AZ_BN)$sulfonyl.

The present invention also includes a compound of formula (III),

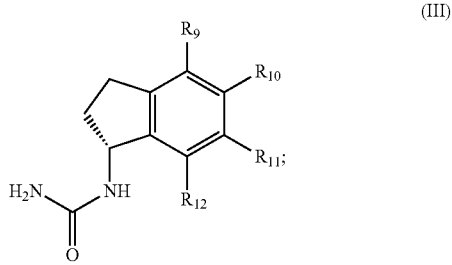

(III)

wherein $R_9$, $R_{10}$, $R_{11}$, and $R_{12}$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, aryl, carboxy, carboxyalkyl, cyano, cyanoalkyl, formyl, formylalkyl, haloalkoxy, haloalkyl, haloalkylthio, halogen, heteroaryl, heterocycle, hydroxy, hydroxyalkyl, mercapto, mercaptoalkyl, nitro, $(CF_3)_2(HO)C-$, $R_B(SO)_2R_AN-$, $R_AO(SO)_2-$, $R_BO(SO)_2-$, $Z_AZ_BN-$, $(Z_AZ_BN)$alkyl, $(Z_AZ_BN)$carbonyl, $(Z_AZ_BN)$carbonylalkyl, and $(Z_AZ_BN)$sulfonyl.

The present invention also includes a composition, comprising a compound of formula (Xa), a compound of formula (Xb), or a mixture thereof, wherein Y is chloro or bromo,

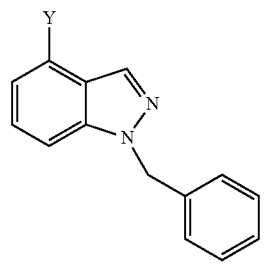

(Xa)

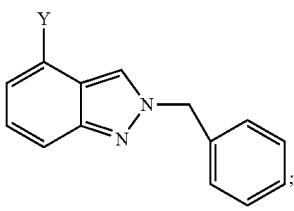

(Xb)

which is useful in the process of preparing a compound of formula (IX). The present invention further includes a compound of formula (XI),

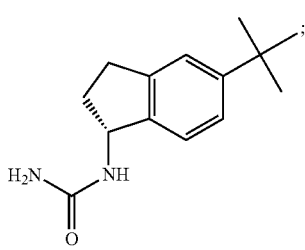

(XI)

which is useful in the process of preparing a compound of formula (IX). It is understood that the compounds of formula (IIa), (IIa$_1$), (IIb), (IIb$_2$) and (III), are useful in the process of preparing a compound of formula (I), which is representative of compounds of the present invention, and which is useful for the treatment of a disorder by inhibiting vanilloid receptor subtype 1 in a mammal comprising administering a therapeutically effective amount of a compound of formula (I) or a pharmaceutically acceptable salt or prodrug thereof. It is understood that the disorder includes pain, inflammatory hyperalgesia, urinary incontinence and bladder overreactivity. It is also understood that the compounds of formula (Xa), (Xb), (Xc), (Xd) and (XI), are useful in the process of preparing a compound of formula (IX), which is useful for the treatment of a disorder by inhibiting vanilloid receptor subtype 1 in a mammal comprising administering a therapeutically effective amount of a compound of formula (I) or a pharmaceutically acceptable salt or prodrug thereof. It is understood that the disorder includes pain, inflammatory hyperalgesia, urinary incontinence and bladder overreactivity.

DEFINITIONS

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through an alkoxy group, as defined herein. Representative examples of alkoxyalkoxy include, but are not limited to, methoxymethoxy, ethoxymethoxy and 2-ethoxyethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylsulfanyl, ethylsulfanyl, tert-butylsulfanyl, and hexylsulfanyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means a phenyl group, or a bicyclic or a tricyclic fused ring system wherein one or more of the fused rings is a phenyl group. Bicyclic fused ring systems are exemplified by a phenyl group fused to a cycloalkyl group, as defined herein, or another phenyl group. Tricyclic fused ring systems are exemplified by a bicyclic fused ring system fused to a cycloalkyl group, as defined herein, or another phenyl group. Representative examples of aryl include, but are not limited to, anthracenyl, azulenyl, fluorenyl, indenyl, naphthyl, phenyl and tetrahydronaphthyl.

The aryl groups of this invention are optionally substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $Z_CZ_DN$—, $(Z_CZ_DN)$alkyl, $(Z_CZ_DN)$carbonyl, $(Z_CZ_DN)$carbonylalkyl, $(Z_CZ_DN)$sulfonyl, —$NR_AS(O)_2R_B$, —$S(O)_2OR_A$ and —$S(O)_2R_A$ wherein $R_A$ and $R_B$ are as defined herein.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "carboxy" as used herein, means a —$CO_2H$ group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" as used herein, means a saturated monocyclic ring system containing from 3 to 8 carbon atoms. Examples of cycloalkyl include cyclopropyl, cyclobutyl, cyclopentyl, cyclohexyl, cycloheptyl, and cyclooctyl.

The term "cycloalkylalkyl" as used herein, means a cycloalkyl group, as defined herein, appended to the parent molecular moiety through an alkyl group, as defined herein.

The term "ethylenedioxy" as used herein, means a —$O(CH_2)_2O$— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "formylalkyl" as used herein means a formyl group, as defined herein, appended to the parent molecular moiety through an alkyl group, as defined herein.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl trifluoromethyl, pentafluoroethyl, and 2-chloro-3-fluoropentyl.

The term "haloalkylthio" as used herein, means at least one halogen, as defined herein, appended to the parent molecular moiety through an alkylthio group, as defined herein. Representative examples of haloalkylthio include, but are not limited to, trifluoromethylthio.

The term "heteroaryl," as used herein, means a monocyclic heteroaryl or a bicyclic heteroaryl. The monocyclic heteroaryl is a 5 or 6 membered ring containing at least one heteroatom independently selected from the group consisting of O, N, and S. The 5 membered ring contains two double bonds may contain one, two, three or four nitrogen atoms, one nitrogen atom and one oxygen atom, one nitrogen atom and one sulfur atom, or one oxygen atom or one sulfur atom. The 6 membered ring contains three double bonds may contain one, two, three or four nitrogen atoms, one nitrogen atom and one oxygen atom, one nitrogen atom and one sulfur atom, one or two oxygen atoms or one or two sulfur atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl. Representative examples of bicyclic heteroaryl include, but are not limited to, benzimidazolyl, benzofuranyl, benzothienyl, benzoxadiazolyl, cinnolinyl, dihydroquinolinyl, dihydroisoquinolinyl, furopyridinyl, indazolyl, indolyl, isoquinolinyl, naphthyridinyl, quinolinyl, tetrahydroquinolinyl, and thienopyridinyl.

The heteroaryl groups of this invention are optionally substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $Z_CZ_BN$—, $(Z_CZ_BN)$alkyl, $(Z_CZ_BN)$carbonyl, $(Z_CZ_BN)$carbonylalkyl, $(Z_CZ_BN)$sulfonyl, —$NR_AS(O)_2R_B$, —$S(O)_2OR_A$ and —$S(O)_2R_A$ wherein $R_A$ and $R_B$ are as defined herein.

The term "heterocycle," as used herein, refers to a three, four, five, six, seven, or eight membered ring containing one or two heteroatoms independently selected from the group consisting of nitrogen, oxygen, and sulfur. The three membered ring has zero double bonds. The four and five membered ring has zero or one double bond. The six membered ring has zero, one, or two double bonds. The seven and eight membered rings have zero, one, two, or three double bonds. The heterocycle groups of the present invention can be attached to the parent molecular moiety through a carbon atom or a nitrogen atom. Representative examples of heterocycle include, but are not limited to, azabicyclo[2.2.1]heptanyl, azabicyclo[2.2.1.]octanyl, azetidinyl, hexahydro-1H-azepinyl, hexahydroazocin-(2H)-yl, indazolyl, morpholinyl, octahydroisoquinoline, piperazinyl, piperidinyl, pyridinyl, pyrrolidinyl, and thiomorpholinyl.

The heterocycles of the present invention are optionally with substituted with 1, 2, 3, or 4 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkynyl, carboxy, cyano, formyl, haloalkoxy, haloalkyl, halo, hydroxy, hydroxyalkyl, mercapto, nitro, piperidinyl, and oxo.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy" as used herein, means a —OCH$_2$O— group wherein the oxygen atoms of the methylenedioxy are attached to the parent molecular moiety through two adjacent carbon atoms.

The term "nitro" as used herein, means a —NO$_2$ group.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl). Methods describing how to introduce or remove such groups are outlined in Protecting Groups In Organic Synthesis, 3$^{rd}$ Ed. Theodora W. Greene and Peter G. M. Wuts, John Wiley & Sons, Inc., or as known to one skilled in the art.

The term "oxo" as used herein, means =O.

The term "P—Z," as used herein, means a nitrogen protecting group, selected from the group consisting of alkoxyalkyl, alkylcarbonyl, alkoxycarbonyl, arylalkyl, arylcarbonyl and aryloxycarbonyl. Preferred P groups include but are not limited to alkylcarbonyl, alkoxycarbonyl, arylalkyl and aryloxycarbonyl.

The term "$R_A$," as used herein, means a substituent that is selected from the group consisting of hydrogen and alkyl.

The term "$R_B$," as used herein, means a substituent that is selected from the group consisting of alkyl, aryl, and arylalkyl.

The term "sulfonyl" as used herein, means a —S(O)$_2$— group.

The term "$Z_AZ_BN$—" as used herein, means two groups, $Z_A$ and $Z_B$, which are appended to the parent molecular moiety through a nitrogen atom. $Z_A$ and $Z_B$ are each independently selected from hydrogen, alkyl, alkylcarbonyl, formyl, aryl and arylalkyl. Representative examples of $Z_AZ_BN$— include, but are not limited to, amino, methylamino, acetylamino, benzylamino, phenylamino, and acetylmethylamino.

The term "($Z_AZ_BN$)alkyl" as used herein, means a $Z_AZ_BN$— group, as defined herein, appended to the parent molecular moiety through an alkyl group, as defined herein. Representative examples of ($Z_AZ_BN$)alkyl include, but are not limited to, aminomethyl, 2-(methylamino)ethyl, 2-(dimethylamino)ethyl and (ethylmethylamino)methyl.

The term "($Z_AZ_BN$)carbonyl" as used herein, means a $Z_AZ_BN$— group, as defined herein, appended to the parent molecular moiety through a carbonyl group, as defined herein. Representative examples of ($Z_AZ_BN$)carbonyl include, but are not limited to, aminocarbonyl, (methylamino)carbonyl, (dimethylamino)carbonyl and (ethylmethylamino)carbonyl.

The term "($Z_AZ_BN$)carbonylalkyl" as used herein, means a ($Z_AZ_BN$)carbonyl group, as defined herein, appended to the parent molecular moiety through an alkyl group, as defined herein. Representative examples of ($Z_AZ_BN$)carbonylalkyl include, but are not limited to, (aminocarbonyl)methyl, 2-((methylamino)carbonyl)ethyl and ((dimethylamino)carbonyl)methyl.

The term "($Z_AZ_BN$)sulfonyl" as used herein, means a $Z_AZ_BN$— group, as defined herein, appended to the parent molecular moiety through a sulfonyl group, as defined herein. Representative examples of ($Z_AZ_BN$)sulfonyl include, but are not limited to, aminosulfonyl, (methylamino)sulfonyl, (dimethylamino)sulfonyl and (ethylmethylamino)sulfonyl.

The term "$Z_CZ_DN$—" as used herein, means two groups, $Z_C$ and $Z_D$, which are appended to the parent molecular moiety through a nitrogen atom. $Z_C$ and $Z_D$ are each independently selected from hydrogen, alkyl, alkylcarbonyl, formyl, aryl and arylalkyl. Representative examples of $Z_CZ_DN$— include, but are not limited to, amino, methylamino, acetylamino, benzylamino, phenylamino, and acetylmethylamino.

The term "($Z_CZ_DN$)alkyl" as used herein, means a —N$Z_CZ_D$ group, as defined herein, appended to the parent molecular moiety through an alkyl group, as defined herein. Representative examples of ($Z_CZ_DN$)alkyl include, but are not limited to, aminomethyl, 2-(methylamino)ethyl, 2-(dimethylamino)ethyl and (ethylmethylamino)methyl.

The term "($Z_CZ_DN$)carbonyl" as used herein, means a $Z_CZ_DN$— group, as defined herein, appended to the parent molecular moiety through a carbonyl group, as defined herein. Representative examples of ($Z_CZ_DN$)carbonyl include, but are not limited to, aminocarbonyl, (methylamino)carbonyl, (dimethylamino)carbonyl and (ethylmethylamino)carbonyl.

The term "($Z_CZ_DN$)carbonylalkyl" as used herein, means a ($Z_CZ_DN$)carbonyl group, as defined herein, appended to the parent molecular moiety through an alkyl group, as defined herein. Representative examples of ($Z_CZ_DN$)carbonylalkyl include, but are not limited to, (aminocarbonyl)methyl, 2-((methylamino)carbonyl)ethyl and ((dimethylamino)carbonyl)methyl.

The term "$(Z_CZ_DN)$sulfonyl" as used herein, means a $Z_CZ_DN$— group, as defined herein, appended to the parent molecular moiety through a sulfonyl group, as defined herein. Representative examples of $(Z_CZ_DN)$sulfonyl include, but are not limited to, aminosulfonyl, (methylamino)sulfonyl, (dimethylamino)sulfonyl and (ethylmethylamino)sulfonyl.

Compounds of the present invention were named by ACD/ChemSketch version 5.0 (developed by Advanced Chemistry Development, Inc., Toronto, ON, Canada) or were given names that appeared to be consistent with ACD nomenclature.

Schemes

The compounds of the invention can be better understood in connection with the following synthetic schemes and following methods that illustrate a means by which the compounds can be prepared.

Abbreviations which have been used in the descriptions of the schemes and the examples that follow are: DME for 1,2-dimethoxyethane or ethylene glycol dimethyl ether, DMF for N,N-dimethylformamide, DMSO for dimethyl sulfoxide, LDA for lithium diisopropylamide which can be prepared by the slow addition of 2.5 N butyllithium in hexanes to a solution of diisopropylamine in THF between 0° C. and −75° C., MTBE for methyl tert-butylether, THF for tetrahydrofuran, rt for "room temperature" or ambient temperature suitably ranging from about 20° C. to about 30° C.

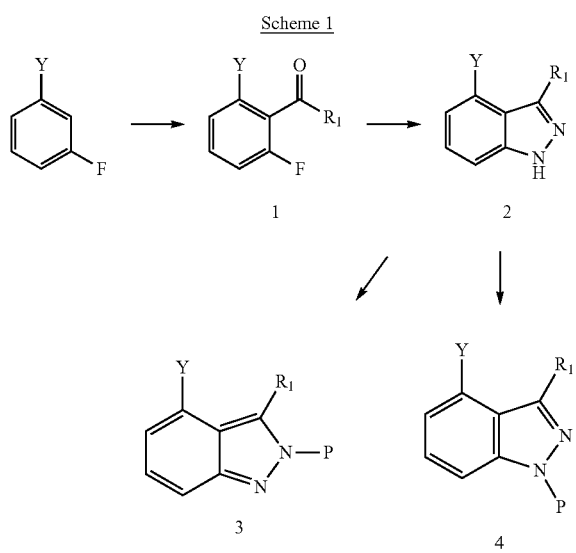

Scheme 1

As shown in Scheme 1, halofluorobenzene, wherein the halo of halofluorobenzene, Y, is either chloro or bromo, when treated with base including, but not limited to, lithium diisopropylamide (LDA), lithium dicyclohexyamide or an equivalent as known to one skilled in the art, in a solvent such as but not limited to tetrahydrofuran, methyl tert-butyl ether or diethyl ether, between the temperature of about −50° C. to about −78° C. for about 1 to about 3 hours; followed by treatment with compounds of formula $R_1C(\!=\!O)\!-\!X$, wherein $R_1$ is hydrogen, alkenyl or alkyl, and X is chloro, $(CH_3)_2N$—, phenoxy, or nitrophenoxy, will provide compounds of formula 1. In the instance where X is $(CH_3)_2N$—, the workup is generally accompanied by the addition of an acid such as acetic acid or a dilute aqueous mineral acid. More preferred conditions include, the use of lithium diisopropylamide in tetrahydrofuran at a temperature between about −70° C. to about −78° C. for about 1 hour, followed by the addition of $R_1C(\!=\!O)\!-\!X$, followed by the addition of an acid such as acetic acid or a dilute aqueous mineral acid, allowing the mixture to come to ambient temperature, followed by partitioning between an aqueous and organic solvent, followed by separation of the organic solution and concentration. Compounds of formula 1 when treated with anhydrous hydrazine, or hydazine hydrate under heated conditions will provide indazoles of formula 2. Conditions for the cyclization include heating to between about 50° C. to about 100° C., a mixture of the compound of formula 1 with anhydrous hydrazine or hydrazine hydrate in a solvent including but not limited to DMF, DMSO or THF. Alternatively, compounds of formula 1 containing a hydrogen atom in the $R_1$, may be complexed with hydroxylamine or O-alkylated hydroxylamine to form the corresponding oxime. The oxime may stabilize the formyl group of compounds of formula 1. The oxime may be utilized directly, to form the indazole by heating in the presence of hydrazine to provide compounds of formula 2. Compounds of formula 2 when treated with reagents which will react with nitrogen atoms to protect them from further reactions, for example P—Z, which include acetyl chloride, acetic anhydride, benzyl chloroformate, di-tert-butyl dicarbonate or 9-fluorenylmethyl chloroformate, will provide either the compound of formula (3), the compound of formula (4) or a mixture of both the compound of formula (3) and the compound of formula (4) depending on the conditions utilized. Often a mixture containing a majority of one product versus the other may be obtained, which can be further purified to isolate one compound from the other or at least obtain a mixture which has been enriched in one of the compounds. A preferred protecting group for the nitrogen atom of the compounds of formula 2 is benzyl or a substituted benzyl (F, OMe etc.). Compounds of formula 2 when treated with benzyl bromide under specific heated conditions will provide high yields of either compound of formula 3 or compound of formula 4, wherein P is benzyl, depending on conditions utilized. Recrystallization of the mixtures of products will reduce the quantity of the one of the compounds to provide a highly enriched or pure sample of the either the N-1 protected isomer (compound of formula 4) or N-2 protected isomer (compound of formula 3), depending on the conditions and product desired. In general, the compound of formula 4 is obtained by heating the mixture of compound of formula 2 with benzyl bromide to the temperature between about 105° C. to about 115° C. for between 20-24 hours, whereas the compound of formula 3 is obtained by heating the mixture of compound of formula 2 with benzyl bromide to the temperature between about 50° C. to about 60° C. for about 20-24 hours. The reaction is typically conducted in a solvent such as but not limited to DMF.

Scheme 2

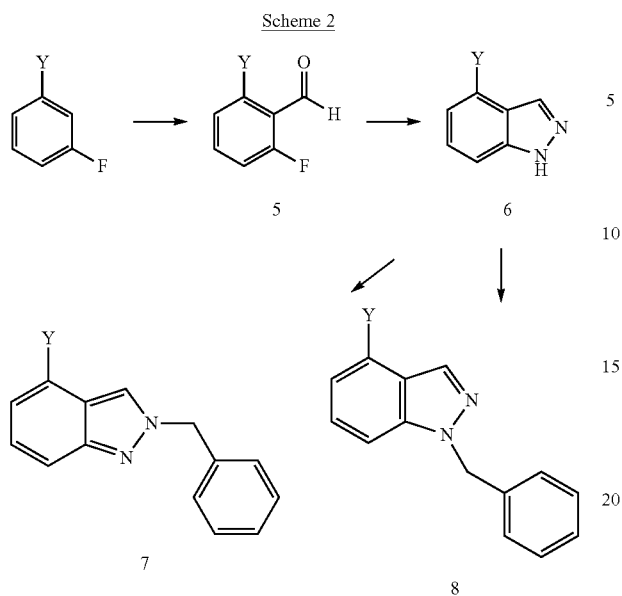

Scheme 3

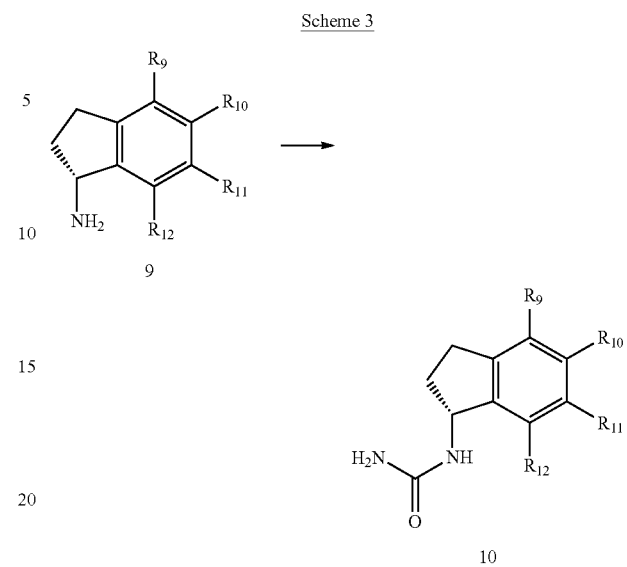

Similarly, compounds of formula 7 and 8 can be obtained according to Scheme 2. The use of N,N-dimethyl formamide as the compound of formula $R_1C(=O)$—X, followed by an acidic workup, such as stirring in the presence of acetic acid will provide the compound of formula 1, wherein the $R_1$ group is formyl. When halofluorobenzene, wherein the halo Y is chloro or bromo, is treated with LDA, followed by the addition of DMF, optionally followed by an acidic workup will provide compounds of formula 5. Compounds of formula 5 when treated with hydrazine hydrate under heated conditions will provide indazoles of formula 6. Alternatively, compounds of formula 5 when treated with hydroxylamine or O-substituted hydroxylamine will provide the corresponding oxime, which may be then treated with hydrazine under heated conditions will provide indazoles of formula 6. Compounds of formula 6 when treated with benzyl bromide under specific heated conditions, as outlined in Scheme 1, will provide high yields of either compound of formula 7 or compound of formula 8 depending on conditions. Recrystallization of the products will reduce the quantity of the undesired isomers depending on the conditions and product desired.

As outlined in Scheme 3, compounds of formula 9, wherein $R_9$, $R_{10}$, $R_{11}$ and $R_{12}$ $R_9$, $R_{10}$, $R_{11}$, and $R_{12}$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, aryl, carboxy, carboxyalkyl, cyano, cyanoalkyl, formyl, formylalkyl, haloalkoxy, haloalkyl, haloalkylthio, halogen, heteroaryl, heterocycle, hydroxy, hydroxyalkyl, mercapto, mercaptoalkyl, nitro, $(CF_3)_2(HO)C$—, $R_B(SO)_2R_AN$—, $R_AO(SO)_2$—, $R_BO(SO)_2$—, $Z_AZ_BN$—, $(Z_AZ_BN)$alkyl, $(Z_AZ_BN)$carbonyl, $(Z_AZ_BN)$carbonylalkyl, and $(Z_AZ_BN)$sulfonyl, which are made according to the procedure previously reported in US 2005/0043351A1, when treated with phenyl carbamate or a similar reagent will provide compounds of formula 10. Preferred conditions include the treatment of compounds of formula 9 with phenyl carbamate in the presence of a base such as but not limited to triethylamine, diisopropylethylamine, N-methyl morpholine, sodium carbonate or potassium carbonate in a solvent such as but not limited to THF, acetonitrile or DMF. More preferred conditions are when a mixture of a compound of formula 9, phenyl carbamate and diisopropylethylamine are refluxed together in THF for between about 2 hours to about 10 hours.

Scheme 4

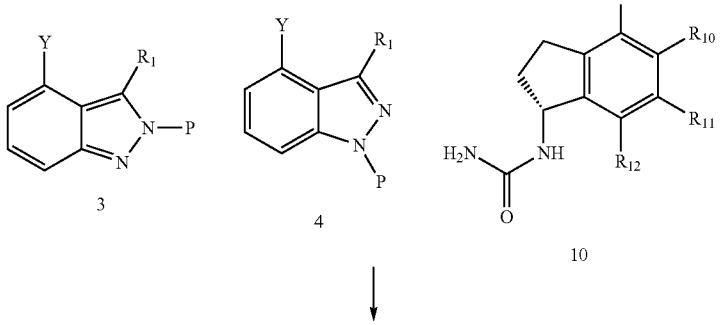

-continued

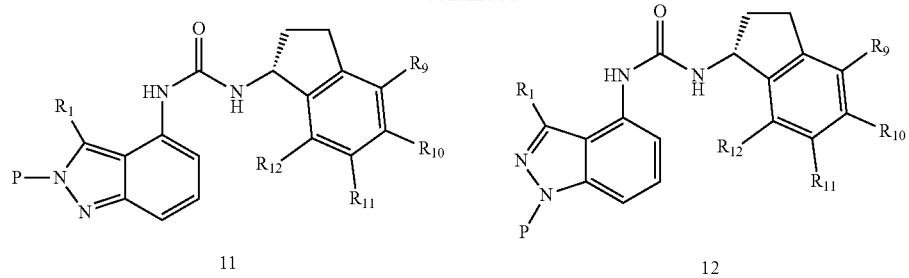

11

12

As shown in Scheme 4, the treatment of a mixture of a compound of formula 10, a base consisting of potassium phosphate, potassium carbonate or cesium carbonate and a compound of formula 3, a compound of formula 4 or a mixture of both, wherein Y is chloro or bromo, in the presence of a catalyst prepared from a palladium compound, preferably palladium acetate or $Pd_2(DBA)_3$ and a phosphine based ligand, including but not limited to Xantphos, 2-di-t-butylphosphino-1-1'-binaphthyl, 5-(di-t-butylphosphanyl)-1', 3',5'-triphenyl-1'H-[1,4']bipyrazolyl, will provide either the compound of formula 11, the compound of formula 12, or a mixture of both compounds of formula 11 and compound of formula 12. The reaction is usually conducted in a solvent such as but not limited to ethylene glycol dimethyl ether. Preferably, the reaction is carried out using cesium carbonate as the base and heated to reflux for about 3 to about 20 hours. More preferably, the reaction is heated to reflux for 5-10 hours. The reaction may be filtered to remove insoluble material to simplify the isolation of the product, and often following concentrating the volume of the mixture under reduced pressure, the product may be isolated following dilution with another solvent such as hexane, heptane and the like followed by filtration of the compounds of formula 11 and/or 12.

As shown in Scheme 5, either the compounds of formula 11, the compounds of formula 12 or a mixture of both when treated according to conditions known to remove the nitrogen protecting group, or as outline in Protecting Groups In Organic Synthesis, $3^{rd}$ Ed. Theodora W. Greene and Peter G. M. Wuts, John Wiley & Sons, Inc., will provide the compound of formula 13 which is representative of compounds of formula (I). For example, when the protecting group is benzyl, the removal may be effected by treatment with a palladium catalyst in the presence of a hydrogen donor comprising an atmosphere of hydrogen, formic acid, or cyclohexadiene in a solvent comprising alcoholic solvents, tetrahydrofuran or ethyl acetate; to provide the compound of formula 13. Examples of palladium catalyst include but are not limited to 5-20% palladium on carbon, palladium hydroxide or palladium on barium sulfate. Typical solvents include methanol, ethanol, tetrahydrofuran, ethyl acetate and the like. Often acetic acid may be utilized to increase the rate of reaction. Preferably, 20% palladium hydroxide and formic acid in tetrahydrofuran effects the transformation. More preferably, the heating of the compounds of formula 11 and/or 12 in the presence of 20% palladium hydroxide and formic acid in tetrahydrofuran to 60° C. for about 1-5 hours will provide the compound of formula 13.

Scheme 5

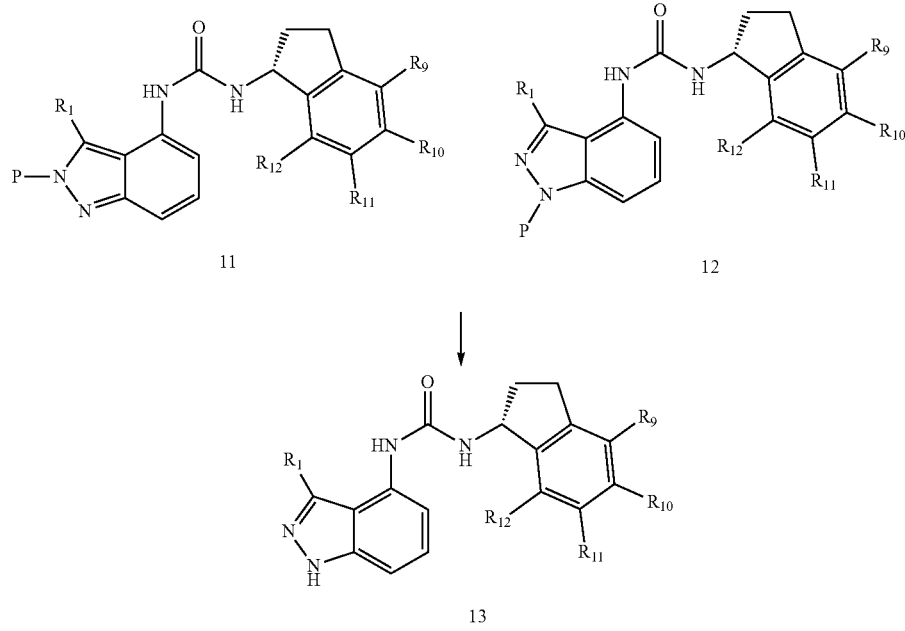

EXAMPLES

The following Examples are intended as an illustration of and not a limitation upon the scope of the invention as defined in the appended claims.

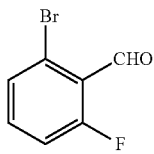

Example 1

2-Bromo-6-fluorobenzaldehyde

1-Bromo-3-fluorobenzene (17.3 g, 0.1 M) was added over 5 minutes to a solution of lithium diisopropylamide (prepared from 11.5 g, 0.1 M diisopropylamine and 40 mL, 2.5 N butyllithium in hexanes) in THF between −70 and −75° C. After stirring for 1 hour at −75° C., DMF (8 mL) was added to the mixture over 10 minutes. The stirring was continued cold for additional 40 minutes after which the mixture was quenched by addition of acetic acid (26 g). The mixture was allowed to warm to ambient temperature and transferred into the mixture of 200 mL MTBE, 200 mL water and 150 mL hydrochloric acid (~4 N). The organic layer was separated and concentrated in vacuo to provide the desired bromofluorobenzaldehyde (19.2 g, 95%): $^1$H NMR (CDCl$_3$, δ, ppm) 7.14 (t, 1H, J=7.6 Hz), 7.39 (m, 1H), 7.48 (d, 1H, J=7.5 Hz), 10.34 (s, 1H).

Example 2

4-Bromoindazole

Direct Preparation.

To a stirred solution of bromofluorobenzaldehyde (20.3 g, 0.1 mol) in DMSO (20 mL) at room temperature is added hydrazine monohydrate (100 mL) while maintaining the internal temperature less than 35° C. The mixture is then heated to 70-75° C. for 22 hours after which the internal temperature is adjusted to 25° C. The mixture was diluted with water (125 mL) followed by heptanes (25 mL) while maintaining the internal temperature less than 40° C. The mixture was stirred at ambient temperature for 1 hour and the product slurry was filtered to collect the solids. The wet cake was washed with 4:1 H$_2$O/MeOH (2×20 mL), then dried at 50° C. in a vacuum oven to provide 14.7 g (75%) of the titled compound: $^1$H NMR (DMSO-d$_6$, δ, ppm) 7.28 (t, 1H, J=7.6 Hz), 7.34 (d, 1H, J=7.4 Hz), 7.59 (d, 1H, J=7.5 Hz), 8.05 (s, 1H), 13.46 (s, 1H, —NH).

Preparation Via Oxime Intermediate.

Hydroxylamine (50% in water, 7 g, 0.1 mol) was added to a solution of bromofluorobenzaldehyde (20.3 g, 0.1 mol) in dioxane (50 mL) while maintaining an internal temperature less than 30° C. After 30 minutes, hydrazine monohydrate (50 mL) was added to the mixture and the mixture was heated to reflux (85° C.) for 24 hours. The mixture was cooled to 25° C. and concentrated under reduced pressure to a volume of about 50 mL. The mixture was diluted with water (100 mL) while maintaining the internal temperature less than 40° C. The mixture was stirred at ambient temperature for at least 1 hour. The product slurry was filtered to collect the solids. The wet cake was washed with 4:1 H$_2$O/MeOH (2×20 mL), dried in at 50° C. in a vacuum oven to provide 14.9 g (76%) of the titled compound.

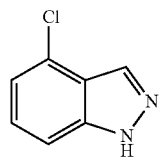

Example 3

4-Chloroindazole

4-Chloroindazole could be prepared according to the procedure of Example 2 substituting 2-chloro-6-fluorobenzaldehyde for 2-bromo-6-fluorobenzaldehyde as a starting material. Isolated yield 70-74%: $^1$H NMR (CDCl$_3$, δ, ppm) 7.15 (d, 1H, J=7.4 Hz), 7.30 (t, 1H, J=7.6 Hz), 7.40 (d, 1H, J=7.5 Hz), 8.16 (s, 1H), 10.61 (s, 1H, —NH).

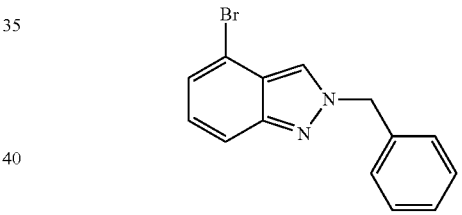

Example 4

2-N-benzyl-4-bromoindazole

4-Bromoindazole of Example 2 (17.4 g, 0.088 M), benzyl bromide (22.7 g, 0.132 M) and DMF (35 mL) were heated to about 50° C. for 25 hours (HPLC: 15:1 ratio of 2-N and 1-N isomers). The mixture was cooled to ambient temperature and diluted with ethyl acetate (160 mL) and water (100 mL). The organic layer was separated, washed with aqueous sodium bicarbonate (5%, 100 mL). The organic layer was separated and concentrated under reduced pressure. The residue was diluted with isopropanol (160 mL) and concentrated under reduced pressure to a volume of about 120 mL. The mixture was heated to 50° C. to dissolve the solid and diluted with water (70 mL) to precipitate the product. The slurry was cooled to 0° C. and the precipitate was filtered off. The solid was washed with a mixture of IPA and Water (1:1, 50 mL), and dried at 50° C. to provide the titled compound (16.5 g, 77%, which contained less than 2% of 1-N-isomer by HPLC): $^1$H NMR (CDCl$_3$, δ, ppm) 5.56 (s, 2H), 7.11 (m, 1H), 7.21 (d, J=7.2 Hz, 1H), 7.24-7.39 (m, 5H), 7.65 (d, J=8.6 Hz, 1H), 7.88 (s, 1H).

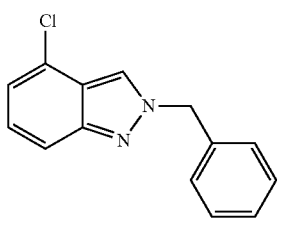 [SMILES: Clc1cccc2nn(Cc3ccccc3)cc12]

Example 5

2-N-benzyl-4-chloroindazole

2-N-benzyl-4-chloroindazole is prepared according to the procedure of Example 4 by substituting Example 3 for Example 4 (62% yield). $^1$H NMR (CDCl$_3$, δ, ppm) 5.69 (s, 2H), 7.06 (d, J=7.3 Hz 1H), 7.21 (d,d J=7.2, 8.6 Hz, 1H), 7.30-7.40 (m, 5H), 7.62 (d, J=8.6 Hz, 1H), 7.95 (s, 1H).

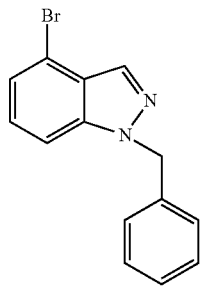 [SMILES: Brc1cccc2c1cnn2Cc1ccccc1]

Example 6

1-N-benzyl-4-bromoindazole

4-Bromoindazole of Example 2 (14.8 g, 0.075 M), benzyl bromide (14.8 g, 0.086 M) and DMF (30 mL) were heated to 110° C. for 22 hours (HPLC: 19:1 ratio of 1-N and 2-N isomers). The mixture was cooled to ambient temperature and diluted with ethyl acetate (75 mL), heptanes (75 mL) and water (75 mL). The organic layer was separated and washed with aqueous sodium bicarbonate (5%, 75 mL). The organic layer was separated and concentrated under reduced pressure. The residue was dissolved in methanol (100 mL) and the product was precipitated with water (100 mL). Filtration and drying under reduced pressure at 50° C. provided the 1-N isomer (15.0 g, 70%, less than 5% of 2-N isomer by HPLC): $^1$H NMR (CDCl$_3$, δ, ppm) 5.56 (s, 2H), 7.10-7.18 (m, 3H), 7.23-7.32 (m, 5H), 8.04 (s, 1H).

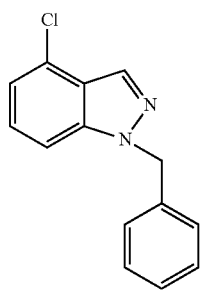 [SMILES: Clc1cccc2c1cnn2Cc1ccccc1]

Example 7

1-N-benzyl-4-chloroindazole

1-N-benzyl-4-chloroindazole is prepared according to the procedure of Example 6 by substituting Example 3 for Example 2 (68% yield). $^1$H NMR (CDCl$_3$, δ, ppm) 5.58 (s, 2H), 7.07-7.14 (m, 1H) 7.15-7.20 (m, 2H), 7.20-7.33 (m, 5H), 8.11 (s, 1H)

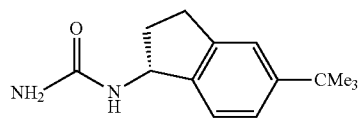

Example 8

(R)-1-(5-tert-butyl-2,3-dihydro-1H-indan-1-yl)urea t-Butyl-indanylamine tosylate (26.5 g, 0.072 M) (as previously reported in US 2005/0043351A1), phenylcarbamate (9.57 g, 0.07 M) and diisopropylethylamine (9.9 g, 0.076 M) in THF (70 mL) were heated to reflux for 15 hours. The mixture was cooled to ambient temperature, diluted with water (140 mL). The product was filtered off and washed with water (100 mL). Drying under reduced pressure at 50° C.-60° C. provided the titled compound (14.7 g, 88%): $^1$H NMR (DMSO-d$_6$, δ, ppm) 1.26 (s, 9H), 1.66 (m, 1H), 2.35 (m, 1H), 2.73 (m, 1H), 2.86 (m, 1H), 4.99 (q, J=7.9 Hz, 1H), 5.41 (s, 2H), 6.21 (d, J=8.4 Hz, 1H), 7.13 (d, J=8.0 Hz, 1H), 7.19-7.23 (m, 2H).

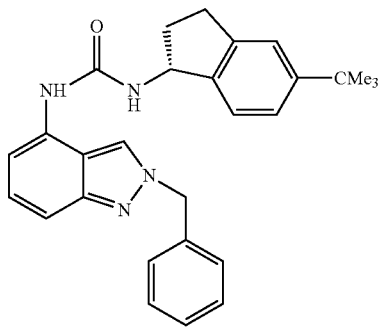

Example 9

(R)-1-(2-benzyl-2H-indazol-4-yl)-3-(5-tert-butyl-2,3-dihydro-1H-indan-1-yl)urea

A solution of 2-N-benzylbromoindazole, Example 4 (5.0 g, 17.4 mmol) in DME (65 mL) was added to a mixture of indanylurea (3.6 g, 15.5 mmol), cesium carbonate (7.5 g), Pd$_2$(DBA)$_3$ (0.23 g) and Xantphos (0.42 g). The mixture was evacuated and purged with nitrogen two times and then refluxed for 5 hours. The mixture was cooled to 70° C. and filtered hot, the solids were washed with hot DME (50 mL). Combined filtrates were concentrated under reduced pressure to about a volume of 50 mL and the product was precipitated by addition of heptane (80 mL). The mixture was filtered, and the wet cake was slurried in ethanol (25 mL). The product was collected by filtration and dried under reduced pressure to provide 5.3 g (70%) of the titled compound: $^1$H NMR (DMSO-d$_6$, δ, ppm) 1.27 (s, 9H), 1.80 (m, 1H), 2.44 (m, 1H), 2.80 (m, 1H), 2.93 (m, 1H), 5.13 (q, J=7.9 Hz, 1H), 5.64 (s, 2H), 6.53 (d, J=8.4 Hz, 1H), 7.09-7.15 (m, 2H), 7.23 (s, 2H), 7.28-7.37 (m, 5H), 7.50 (d, J=6.6 Hz, 1H), 8.23 (s, 1H), 8.43 (s, 1H).

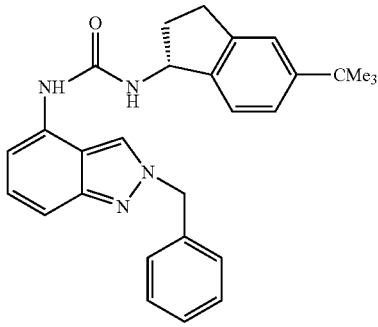

Example 10

An Alternative Method of Obtaining (R)-1-(2-benzyl-2H-indazol-4-yl)-3-(5-tert-butyl-2,3-dihydro-1H-indan-1-yl)urea Prepared from 2-N-benzylchloroindazole In a pressure reactor palladium acetate (29 mg) and 2-di-t-butylphosphino-1-1'-binaphthyl (102 mg) were mixed in dichloromethane (14 ml) at 85° C. for 30 min under inert atmosphere. After the solvent removal by evaporation the reactor was charged with 2-N-benzyl-4-chloroindazole, Example 5 (1.14 g, 4.7 mmol), potassium phosphate (1.36 g, 1.5 eq.), indanylurea (1.0 g, 0.9 eq.), and DME (15 mL) The mixture was evacuated and purged with nitrogen and then heated at 85° C. for 18 hours. The mixture was cooled to 70° C., diluted with DME (50 mL) and filtered hot, the solids were washed with hot DME (50 mL). Combined filtrates were concentrated under reduced pressure to about a volume of 14 mL and the product was precipitated by addition of heptane (22 mL). The product was collected by filtration and dried under reduced pressure to provide 1.6 g (85%) of the titled compound.

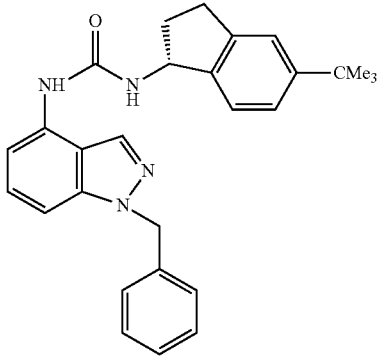

Example 11

(R)-1-(1-benzyl-1H-indazol-4-yl)-3-(5-tert-butyl-2,3-dihydro-1H-indan-2-yl)urea

The titled compound was prepared according to the procedure outlined in Example 9, substituting 1-N-benzyl-4-bromoindazole for 2-N-benzylbromoindazole (60% yield). $^1$H NMR (CDCl$_3$, δ, ppm) 1.29 (s, 9H), 1.80 (m, 1H), 2.63 (m, 1H), 2.83 (m, 1H), 2.92 (m, 1H), 5.25 (d, J=8.3 Hz, 1H), 5.40 (q, J=7.9 Hz, 1H), 5.55 (s, 2H), 6.80 (s, 1H), 7.07 (d, J=7.7 Hz, 1H), 7.15-7.29 (m, 9H), 8.02 (s, 1H).

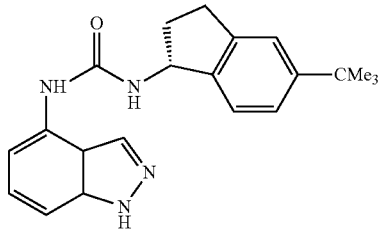

Example 12

1-((R)-5-tert-butyl-2,3-dihydro-1H-inden-1-yl)-3-(3a,7a-dihydro-1H-indazol-4-yl)urea Example 10 (3.0 g), 20% palladium hydroxide on carbon (1.5 g) and formic acid (10 mL) were mixed in THF (100 mL) at 60° C. under nitrogen atmosphere for 3 hours. The mixture was cooled to ambient temperature and filtered. The filtrate was concentrated under reduced pressure and the residue was combined with ethanol (50 mL) and activated carbon (0.5 g). The mixture was refluxed for 1 hour, then filtered. The filtrate was concentrated a volume of 23 mL under reduced pressure and the product was precipitated by the addition of water (8.6 mL). The title compound was filtered and dried to 1.91 g (80% yield).

Alternatively, the title compound could be prepared according to the procedure outlined in Example 12 substituting Example 11 for Example 9.

What is claimed is:

1. A compound of formula (III),

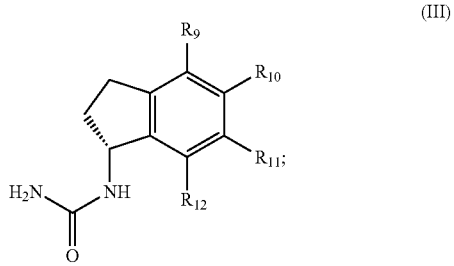

wherein $R_9$, $R_{11}$, and $R_{12}$ are each hydrogen; and $R_{10}$ is selected from the group consisting of alkyl, alkoxy, halogen, hydroxy, cyano, and nitro.

2. A compound of formula (XI),
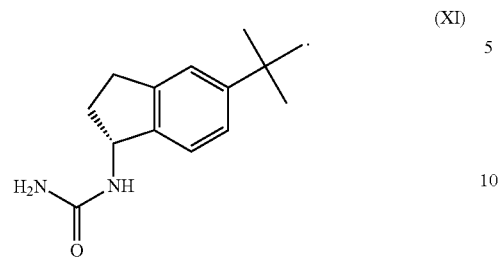
(XI)
* * * * *